United States Patent [19]

Anhäuser et al.

[11] Patent Number: 4,619,253

[45] Date of Patent: Oct. 28, 1986

[54] FOIL- OR FILM-LIKE BANDAGE AND PROCESS FOR USING THE SAME

[75] Inventors: Dieter Anhäuser, Melsbach; Gerhard Kreitlow; Hubertus Olbrich, both of Neuwied; Karl-Heinz Reinhold, Hausen; Anita Schmitt, Rossbach, all of Fed. Rep. of Germany

[73] Assignee: Lohmann GmbH & Co. KG, Neuwied, Fed. Rep. of Germany

[21] Appl. No.: 678,782

[22] Filed: Dec. 6, 1984

[30] Foreign Application Priority Data

Dec. 8, 1983 [DE] Fed. Rep. of Germany ....... 3344334

[51] Int. Cl.[4] ............... A61L 15/00; E04F 15/16; B32B 27/00
[52] U.S. Cl. .................................. 218/156; 428/40; 428/423.1
[58] Field of Search ........................ 128/156

[56] References Cited

U.S. PATENT DOCUMENTS

| | | | |
|---|---|---|---|
| 2,734,503 | 2/1956 | Doyle | 128/156 |
| 2,755,800 | 7/1956 | Thompson | 128/156 |
| 2,817,335 | 12/1957 | Thompson | 128/156 |
| 2,823,672 | 2/1958 | Schladermundt et al. | 128/156 |
| 3,425,412 | 2/1969 | Pope | 128/156 |
| 4,413,621 | 11/1983 | McCracken et al. | 128/156 |
| 4,485,809 | 12/1984 | Dellas | 128/156 |

*Primary Examiner*—Herbert S. Cockeram
*Attorney, Agent, or Firm*—Kerkam, Stowell, Kondracki & Clarke

[57] ABSTRACT

The invention is related to a foil- or film-like bandage consisting of a transparent continuous bandage foil which on the one side is covered with a transparent supporting foil and on the other side is provided with an adhesive layer and a removable cover layer thereupon, the supporting foil extending over said transparent continuous bandage foil at opposite edges and the cover layer having the same size as the adhesive layer, said cover layer having particularly formed preset cuts or preset breaking lines between two points at different edges, preferably opposite edges such that the cover layer is partitioned into two parts and, upon bending of the foil- or film-like bandage, there is produced an auxiliary pull-off means in the cover layer for the same.

11 Claims, 5 Drawing Figures

FOIL- OR FILM-LIKE BANDAGE AND PROCESS FOR USING THE SAME

The invention is related to a medical bandage consisting of a thin transparent foil (bandage foil) which may be fixed to the human or animal body by means of an adhesive layer on the one side thereof. The foil- or film-like bandage may be transparent or not transparent. The present invention is further related to a process for applying such a medical bandage to the substrate.

Adhesive, non-occlusive foil- or film-like bandages have long been used in the medical field. "Non-occlusive" means that the bandage is impermeable to the passage of bacteria and of liquid water but is permeable to oxygen and water vapour. In particular the latter property allows that water vapour produced by the skin may pass through the medical bandage. Such bandages for instance are used for the coverage of injured or burned parts of the skin as incision foil or for the fixing of medical instruments in the skin such as catheters or cannulae.

The transparent polymer bandage foil of the foil- or film-like bandages are continuous, i.e. the bandage foils are not perforated and are not microporous. The adhesive layer fixed to one of its surfaces in the same way has to be water vapour permeable such that the total permeability of the bandage is not smaller than the desired or necessary degree. This prerequisite results in that the foil has to be extremely thin in order to reach the necessary total permeability to water vapour. This results in very thin flexible foils which are characterized by a particularly high flabbiness. There still is another reason why such foils need to be extremely thin. The bandage has to fully follow the shape of the body parts to be covered thereby and this is only possible by a very thin foil. These properties result however in that such bandages are extremely difficult to be applied to the human or animal body, in particular if larger surface areas are to be covered. Thus, to apply such a bandage it is often necessary to have two persons in order to avoid the wrinkling of the foil and sticking of the parts of the adhesive layer to each other. This would result in the bandage being discarded.

Occlusive foil- or film-like bandages are bandages with a very low or even no permeability to water vapour. They are necessary under particular circumstances. They avoid the escaping of water vapour from the skin. Because of the necessity that they closely follow the body shape they are produced from extremely thin, usually transparent foils and are as difficult to be applied to the human body as the non-occlusive bandages.

There are several known bandages which overcome the difficulties of applying such thin foil or film-like bandages to the human body. For instance, U.S. Pat. No. 4,372,303 proposes to apply on the back side of the bandage a stiffening frame as means to assist the application of such bandages which after the application of the bandage is removed again. This proposal may be useful for relatively large bandages. However, the frame operates against to the application of the bandage at body-parts of increased curvature. U.S. Pat. No. 4,374,520 proposes to fix two supporting ledges to the bandage at two opposite edges of the bandage. However, such a bandage cannot be used under all circumstances because of the above given reasons.

A certain advance follows from European patent application No. 0,051,935. The surface of the polymer foil which is not covered with adhesive material is covered by a supporting foil having a somewhat increased stiffness, this supporting foil extending over the area of the polymer foil at one of its edges and thus forms a grasp edge. This supporting foil is only removed after the application of the foil. The adhesive surface of the polymer foil is protected by a cover which also extends at one side over the polymer foil to form a grasp edge. Such a bandage allows certain improvements in its application. It however does not solve all problems because there is provided only one grasp strip at one edge for the supporting foil and therefore again allows contact with the adhesive layer when fixing the bandage to the body areas to be covered. Furthermore, the production of a three layer laminate having an adhesive center layer smaller in area than both covering layers is technically quite difficult and expensive. A certain solution follows from European patent application No. 0,081,987 which shows a polymer foil having two grasp strips at two opposite edges of the foil which grasp strips are free of adhesive material. Said grasp strips may be separated by means of adequate perforation in the foil after the application of the bandage to the body. This allows an easier application of the foil. The problems due to the flabbiness of the foil, as above explained, are not overcome.

The further development of the foil- or film-like bandage as described in European patent application No. 0,081,988 is primarily not in order to ease the application of the bandage but is related to the structure of an absorbing bandage and, thus, is not related to the present application. Contrary thereto, European patent application No. 0,081,989 describes a further embodiment of a foil-or film-like bandage which is claimed to be easier to handle. The coverage of the adhesive layer on the polymer foil has preset cuts such that the central area of the cover may be pulled off leaving a frame like area close to the edges of the cover layer. After the application of the bandage by means of the exposed part of the adhesive layer, it is possible to remove that frame-like part of the cover layer by means of the adhesive polymer foil fixed thereupon due to a respective perforation in the foil- or film-like bandage. This embodiment overcomes the above explained difficulties in the applicatin of the foil but allows only part of the total area of the adhesive polymer foil to be used. It is a further disadvantage that it is technologically quite expensive to produce such a bandage. Easier to handle are polymer foils as described in European patent application No. 0,081,990 which also have a supporting layer on the surface of the foil opposite to the surface provided with an adhesive layer. This layer consists of a woven or non-woven textile material having partitions or extensions, thus giving possibilities to pull off such parts. A similar structure is provided also in the cover layer for the adhesive layer. Such a bandage however does not show lateral grasp edges to handle the textile supporting material. It is recommended to leave the textile material on the bandage even after application. Thus, it is another disadvantage of the described foil- or film-like bandage that the covered area of the body cannot be observed.

There furthermore is known a multilayer foil- or film-like bandage having a supporting layer of paper on a surface of a polymer foil free of adhesive material. The supporting layer is provided with preset cuts such that the central part of the surface may be peeled off before the application of the bandage leaving a window-like central part allowing the exact positioning of the bandage. After the application of the bandage on the body this frame-like strip is removed. This strip stabilizes the polymer foil to a certain extent but it cannot avoid the contact of the adhesive surface during the application of the bandage and, thus, the danger of contamination of the bandage.

Other known embodiments of foil- or film-like bandages of this type are only little different from the above discussed prior art and have the same disadvantages in connection with difficulties in handling the bandage and/or in too difficult a production thereof.

It is therefore an object of the present invention to provide a foil- or film-like bandage which is easy to be produced and overcomes the above discussed difficulties in their use. Furthermore, there is disclosed a method for using the same. The object of the present invention is solved by a foil- or film-like bandage consisting of a transparent continuous bandage foil having a thickness of 10 to 120 μm which on its one side is covered by a transparent supporting foil and on its other side is provided with an adhesive layer which itself is covered by a removable cover layer, wherein the supporting foil extends over the continuous foil at two opposite edges of the foil- or film-like bandage such that it forms two grasp strips and that the cover layer has the same size as the adhesive layer. The cover layer is subdivided by a preset cut or a preset breaking line such into two partial areas, that, due to the geometrical size and form of the preset cut or preset breaking line, for each partial area at least one grasp part is provided by the bending of the foil- or film-like bandage with the formation of a concave curvature of the open surface of the supporting foil if at least two points of attack of the forces producing the bending are distributed on the partial areas of the cover such that the forces attacking vertically to the cover layer through such points thus produce the peel-off of the grasp parts. This means that the preset cut or preset breaking line (1) is positioned such that it preferably runs substantially parallel to the two grasp strips at the opposite edges of the foil- or film-like bandage according to the present invention, and (2) is formed such that, relative to a fictitious straight line substantially between its two end points at the two other opposite edges of the foil- or film-like bandage, preferably substantially in the center of said edges, it extends at least once into each partial area of the cover layer and so burdens at least one grasp part in each partial area of the cover layer.

Preferably the surface area of each individual grasp part is substantially equal in both partial areas of the cover layer, i.e. on both sides of the fictions line of formation of a convex bending of the cover layer, thus producing grasp parts substantially equal size. Upon bending the foil- or film-like bandage with the formation of a convex bending of the cover layer along said fictitious straight connection line between said two end points of said preset cut or preset breaking line, the force due to the sufficiently larger stiffness of the grasp parts over the stiffness of the other layers of the foil- or film-like bandage causes the peel-off of said grasp parts from the adhesive layer.

The invention is illustrated more in detail in the following figures.

Figure 1:
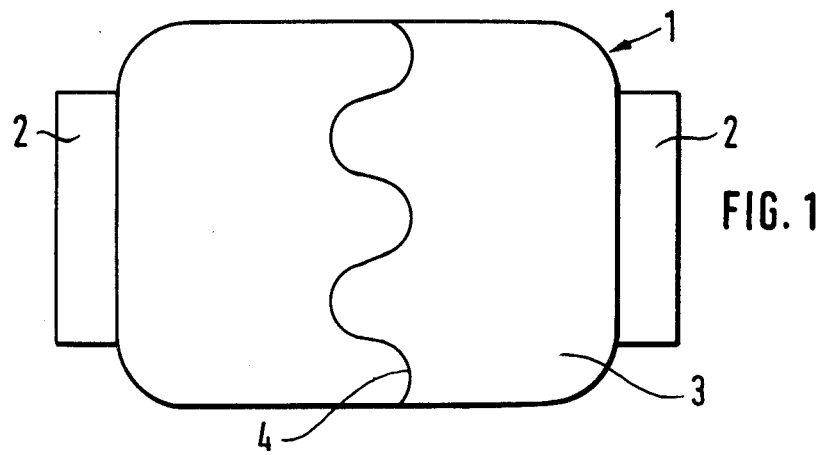
FIG. 1 shows a top plan view of the side of the cover layer of a possible embodiment of the foil- of film-like bandage according to the present invention.

FIG. 1 shows a top view of the foil- or film-like bandage 1 onto the cover layer 3. Extending over the area of the cover layer equal to the area of the polymer foil (not visible in this Figure) are the grasp strips 2 of the supporting foil which are not adhesive. The preset cut or the preset breaking line 4 in a sinoid form is located in the center of the cover layer parallel to the two grasp strips 2 such that there are formed two substantially equal partial surface areas. It follows from FIG. 1 that there are three grasp parts for the left-hand partial area and two grasp parts for the right-hand partial area which are produced by bending the foil- or film-like bandage 1 as above described and peel off from the adhesive layer and allow an easy pull-off of the two partial areas of the cover layer without contacting the adhesive surface. When following this procedure, it is possible to avoid a contarmination of the adhesive surface. It is not necessary that the preset cut or preset breaking line is in the center of the cover layer and may have any suitably geometric form which allows the formation of grasp parts.

Figure 2:
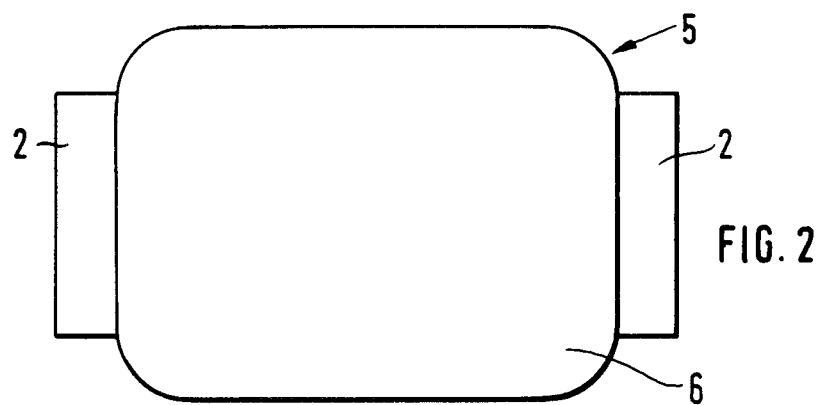
FIG. 2 shows a top view of the adhesive layer of the foil- or film-like bandage after pull-off of the cover layer of the embodiment of FIG. 1.

FIG. 2 shows a top view upon side 6 of the polymer bandage foil 1 covered with an adhesive. As in FIG. 1, there may be seen the grasp strips 2 of the supporting foil still connected with the polymer bandage foil 1. They allow the handling of the polymer bandage foil 1, now ready for application, without any difficulty. It should be noted that this is possible only by the two grasp strips 2 provided on both sides of the bandage foil 1. After the application of the bandage the supporting foil has fulfilled its purpose and may be readily pulled off from the polymer bandage foil 1.

Figure 3:
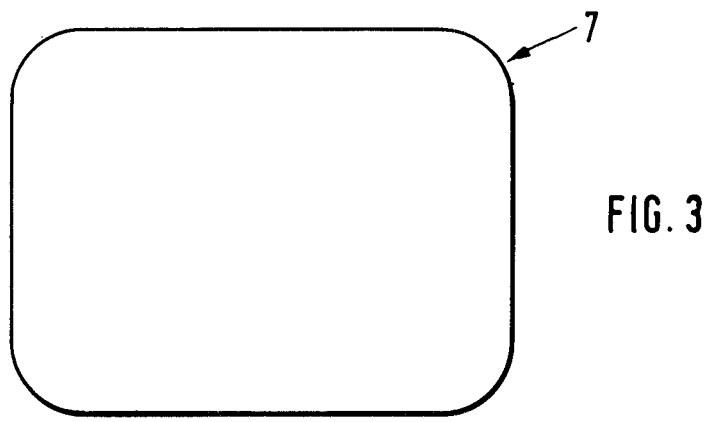
FIG. 3 shows a top view of the bandage foil after its application to a body surface and after removal of the supporting foil.

FIG. 3 shows section 7 of the foil 1 during application after removal of the supporting foil.

Figure 4:
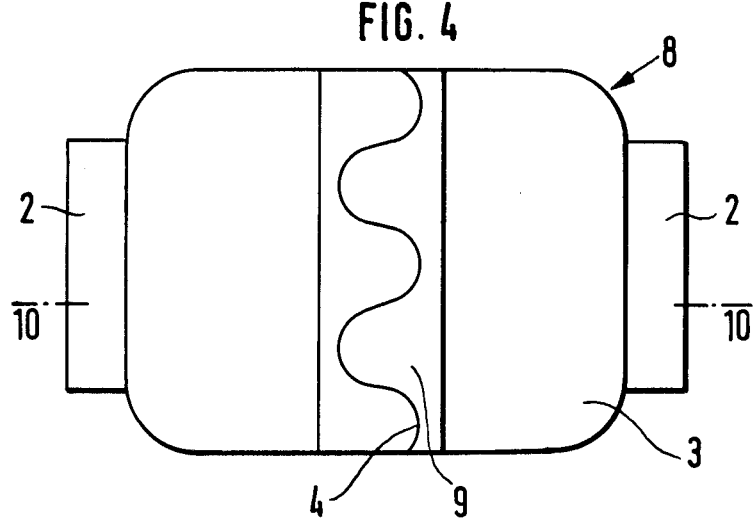
FIG. 4 shows a top view of the side of the cover layer another embodiment of the foil- and film-like bandage according to the present invention.

FIG. 4 shows the top view of the cover layer side of another embodiment of the foil- or film-like bandage 8 according to the present invention. This embodiment is useful and should be used where the difference in the stiffness between the cover layer 3 and the other layers of the foil- of film-like bandage is not sufficient to produce the peel-off of the grasp parts bordered by the preset cut or breaking line 4. Assistance is given by zone 9 having an increased stiffness in the surrounding of the preset cut or preset breaking line assistance in this peel-off procedure.

Figure 5:
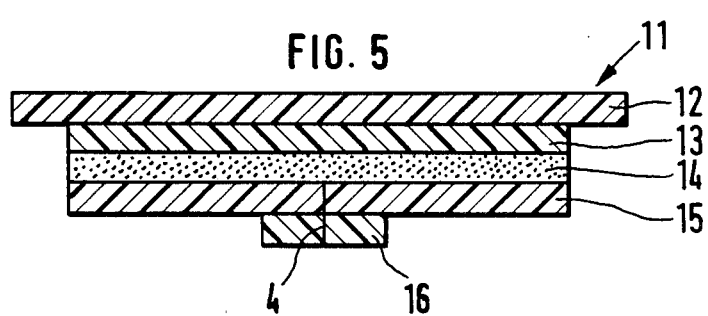
FIG. 5 shows a schematicvertical cut along line 10—10 of FIG. 4 (not true in the scale of FIG. 4).

FIG. 5 further illustrates the constraction of this embodiment, showing schematically (and not true in scale) cross-section 11 along lines 10—10 of FIG. 4. The supporting foil 12 extends on both sides over the area of the polymer bandage foil 13 and thus forms the two grasping strips. The polymer bandage foil 13 is completely covered by the adhesive layer 14 which itself is covered by the cover layer 15. It is a particularity this embodiment that is has a reinforcement strip 16 in the vicinity of the area bordered by the preset cut or the preset breaking line 4. The preset cut or preset breaking line extends through cover layer 15 and reinforcement strip 16 which allows to break both the cover layer 15 and the reinforcement strip 16.

The foil- or film-like bandages are not limited to the form or scale of the example shown in the above figures but may be rendered appropriate to the requests of the user in both respects. However, it should be noted that in all instances the corner parts of the foil- or film-like bandage are rounded in order to prevent an independent peel-off of the bandage at those corners. In general the bandage has to be produced such that the force to pull off the supporting foil from the transparent continuous bandage foil is smaller than the force necessary to pull off the bandage from the body and, on the other hand, the force necessary to pull off the cover layer is smaller than to pull off the supporting layer from the transparent continuous foil.

Useful materials for the transparent supporting foil are known polymers such as polyethylene, polypropylene, polyamide or polyesters. If desired, such supporting foils are covered with a silicon layer on the side towards the continuous transparent bandage foil in order to give the necessary force to separate both foils. The supporting foil may be 20 to 200 μm, preferably 30 to 80 μm thick. The grasp strips should be broad enough to allow a ready handling of the foil. The supporting foil is fixed to the transparent continuous bandage foil not by an adhesive but by means of mechanical adhesion forces as they are produced when the transparent continuous bandage foil is formed at the supporting foil by extrusion, pouring or any other procedure known in the production of foils.

The continuous bandage foil is transparent itself and may be produced by known manners from known polymers. Such polymers are for instance polyurethane, polyvinylchloride, polycinylidenchloride, polyvinylalcohol, polyacrylate, polysulfone, polystyrene, polyethylene, polypropylene, polyamide, ethylen-vinylacetate-copolymers, polyester, polycarbonate, polyvinylfluoride or other fluoro containing polymers.

For the formation of non-occlusive foils polyurethans are most preferred and for occlusive foils polyvinylidenchlorides are preferred. The central transparent continuous bandage foil has a suitable thickness of 10 to 120 μm, preferably 15 to 50 μm. It is preferred that a non-occlusive foil has a water vapour permeability of at least $300 \text{ g} \times \text{m}^{-2} \times 24 \text{ h}^{-1}$.

The adhesive layer is produced from the known, physiologically acceptable adhesive materials. Examples are caoutchouc, rubber-like synthetic homo-, co- or graft polymers, polyacrylates and its copolymers, polyurethanes and silicones. The adhesive material is applied at an area amount of 15 to 80 g/m², preferablly 30 to 50 g/m². There may be included into the adhesive material active agents as they are known in drugs.

The material for the cover layer to the adhesive layer is selected such that its stiffness over the stiffness of the other layers of the foil- or film-like bandage is so large that the described peel-off process for the grasp parts in the partial areas of the cover layer works. In general all materials known in this field are useful for the supporting layer. For instance, there may be used polytetrafluoro- ethylene, cellophane, polyvinylchloride, after-treated paper materials, metallic foils and polymer coated metal foils. The area weight of such materials is 50 to 250 g/m², preferably 80 to 150 g/m². The adhesiveness of the adhesive layer to the cover layer must be such that it allows its removal of the cover layer with a force which is smaller than the force necessary for the removal of the supporting layer from the central continuous bandage foil.

In all cases where the stiffness of the cover layer is too small for the described peel-off mechanism for the grasp parts, the area having the preset cut or the preset breaking lines is reinforced by the provision of a reinforcement strip. This strip is as large as corresponds the area covered by the preset cut or preset breaking line and preferably consists of a usual, unilaterially adhesive material having such a stiffness that the desired peel-off of the grasp parts is obtained. In general, depending upon the material, thicknesses of 30 to 150 μm are sufficient. Furthermore, the area of reinforcement may be produced directly on the cover layer from a liquid, dissolved or dispersed phase by known methods. The so produced foil- or film-like bandage is presented to the user suitably packaged with sterilization (f.i. by gamma-rays) or without sterilization.

The application of the foil- or film-like bandage according to the present invention is carried out such that
(1) the foil is bent with the formation of a concave curvature of the open surface of the supporting foil there are produced forces which cause a peel-off of the at least one grasp part per each partial area of the cover layer formed by the preset cut or preset breaking line,
(2) the partial areas of the cover layer is pulled off from the bandage by grasping the grasp parts,
(3) the now open adhesive layer of the foil- or film-like bandage is fixed onto the intended substrate by grasping the laterally extending grasp strips in the supporting foil and
(4) finally the supporting foil is pulled off from the central continuous bandage foil by grasping one of the two laterally extending grasp strips of the supporting foil.

This method avoids the disadvantages of the known bandages as explained hereinabove and represents an application of foil- or film-like bandages which is all right and safe both in human and veterinary medicine.

The bandages may be produced by methods known to the expert in the art. The following example illustrates the simplicity of the method for producing the foil- or film-like bandage according to the present invention, i.e. the production of a foil- or film-like bandage according to FIG. 4.

EXAMPLE

A solution of a two-component-polyurethane is coated to one side of a polypropylene foil having a thickness of 70 μm and siliconized on the one side, by means of rollers and the solvent is evaporated. Thus, a polyurethane film having a thickness of 35 μm is produced.

In a second step, a paper siliconized unilaterally in known manners and coated with polyethylene, having a surface weight of 120 g/m² is coated with a resin modified polyacrylate adhesive on solvent base per roller coat and by evaporation of the solvent, thus producing an adhesive layer of 40 g/m².

Both the above foils are coated on the each other such that the adhesive layer is on the open side of the polyurethane foil.

The resulting composite foils are cut in a suitable machine to the desired broad web. With the aid of a usual special machine there is provided in this band centrally a unilaterally adhesive polyester adhesive tape (thickness of the polyester foil 30 μm) and thereafter, with control of the depth of the cut, there is provided simultaniously a cut parallel to both edges of the tape and a wave-like sinoid cut in the center of the applied polyester adhesive tape. The cut parallel to both edges of the band extends through the cover layer, the adhesive layer and the polyurethane film allowing to pull off on both sides a lateral strip, leaving the grasp strips on both sides of the supporting foil. The central wave-like sinoid cut extends through the reinforcing adhesive tape, the cover layer and possibly partially through the adhesive layer. After producing the rounded notches forming the rounded corners of the bandage, the band is again collected on rolls and the singular bandage areas are cut on a separate cutting machine. The singular bandage pieces are packed and possibly sterilized in known manners.

What we claim is:

1. A foil- or film-like bandage consisting of a transparent continuous foil or film having a thickness of 10 to 120 μm covered on one side by a transparent supporting foil bonded thereto and on its other side by an adhesive layer which itself is covered by a removable cover layer, said supporting foil extending beyond the edges of the foil or film layer at two opposite edges thereof, thereby forming two grasp strips, said removable cover layer being the same size as the adhesive layer and having a precut or breaking line partitioning said cover layer into two partial areas thereby forming at least one peelable grasp part for each partial area, whereby bending the bandage to a convex curvature of the grasp part area produces peel-off of said grasp parts.

2. Foil- or film-like bandage according to claim 1 wherein a zone of enlarging the stiffness of said cover layer is provided in the cover layer in the surrounding of the precut or preset breaking line to ease the peel-off of said grasp parts from the cover layer when bending the foil- film-like bandage.

3. Foil- or film-like bandage according to claim 1 which is non-occlusive.

4. Foil- or film-like bandage according to claim 1 which is occlusive.

5. Foil- or film-like bandage according to claim 1 wherein the transparent continuous bandage foil has a thickness of 15 to 50 μm.

6. Foil- or film-like bandage according to claim 1 wherein the transparent continuous bandage foil consists of polyurethane.

7. Foil- or film-like bandage according to claim 1 wherein the transparent continuous bandage foil has a watervapour permeability of at least 300 g×m$^{-2}$ ×24 h$^{-1}$.

8. Foil- or film-like bandage according to claim 1 wherein the bandage is constructed in such a way that the force necessary to remove the supporting foil from said transparent continuous bandage foil is smaller then the force necessary to remove the transparent continuous bandage foil from the body.

9. Foil- or film-like bandage according to claim 1 wherein the bandage is constructed in such a way that the force necessary to remove the cover layer is smaller than the force necessary to remove the supporting foil from the transparent continuous bandage foil.

10. Process for the application of a foil- or film-like bandage according to claim 1 wherein the foil- or film-like bandage is bent to form a concave curvature of the open surface of the supporting foil thereby producing forces which peel off the at least one grasp part per partial area of the cover layer, said partial areas of said cover layer being produced by a preset cut or a preset breaking line, said partial areas of said cover layer are removed by means of said grasp parts, said foil- or film-like bandage with its open adhesive layer are grasped at the lateral grasp parts in the supporting foil extending over two opposite edges of the transparent continuous bandage foil, the foil- or film-like bandage is fixed with its adhesive layer to the substrate to be covered by the transparent continuous bandage foil and the supporting foil is pulled off from the transparent continuous bandage foil by means of one of said grasp strips formed by the parts of the supporting foil extending over the opposite edges of the transparent continuous bandage foil.

11. Process according to claim 1 wherein the substrate is a human or animal body.

* * * * *